US006887665B2

(12) United States Patent
Trulson et al.

(10) Patent No.: US 6,887,665 B2
(45) Date of Patent: May 3, 2005

(54) METHODS OF ARRAY SYNTHESIS (75) Inventors: Mark Trulson, San Jose, CA (US); Glenn McGall, Mountain View, CA (US); Jacqueline Fidanza, San Francisco, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/922,426

(22) Filed: Aug. 3, 2001

(65) Prior Publication Data

US 2002/0022721 A1 Feb. 21, 2002

Related U.S. Application Data

(60) Provisional application No. 60/223,290, filed on Aug. 3, 2000.

(51) Int. Cl.$^7$ .......................... C07H 21/04; C07G 1/00
(52) U.S. Cl. .................... 435/6; 435/7.1; 435/DIG. 49; 436/164; 436/524; 436/527; 530/334; 530/335; 536/25.3; 536/25.31
(58) Field of Search ....................... 435/6, 7.1, DIG. 49; 436/164, 524, 527; 536/25.3, 25.31; 530/334, 335

(56) References Cited

U.S. PATENT DOCUMENTS

| | | | |
|---|---|---|---|
| 4,705,729 A | | 11/1987 | Sheats |
| 5,143,854 A | * | 9/1992 | Pirrung et al. ............... 436/518 |
| 5,288,514 A | | 2/1994 | Ellman |
| 6,040,138 A | | 3/2000 | Lockhart et al. |
| 6,083,697 A | | 7/2000 | Beecher et al. |
| 6,159,681 A | * | 12/2000 | Zebala .......................... 435/4 |
| 6,174,998 B1 | | 1/2001 | Muhlegger et al. |
| 6,426,184 B1 | * | 7/2002 | Gao et al. ...................... 435/6 |

FOREIGN PATENT DOCUMENTS

| | | |
|---|---|---|
| WO | WO 97/103 65 A1 | 9/1996 |
| WO | WO 98/20967 A1 * | 5/1998 |

OTHER PUBLICATIONS

Griffling and West IEEE Electron Device Letters EDL–4(1): 14 (1983).
Ghandi, VLSI Fabrication Principles, 1983, Chapter 10.
Hofer et al., Contrast enhanced uv lithography with polysilanes, Advances in Resist Technology, 1984, 108–16, SPIE vol. 489.
Halle, L., et al., J. Vac. Sci. Technol. B., 1985, 323–326, vol. 3(1).
Sheats, et al., J. Vac. Sci. Technol. B., 1985, 323–326, vol. 3(1).
Uchne, et al., Proc. Poly. Mat. Sci. and Eng., 1986, 55, 604–607.
Paul R. West, et al., Contrast Enhanced Photolithography; Application of Photobleaching Processes in Microlithography, J. Imaging Science, Mar./Apr. 1986, 65–68, vol. 20, No. 2.
Don R. Strom, Optical Lithography and Contrast Enhancement, Semiconductor International, May 1986, 182–87.
Endo, et al., High aspect–ratio resist pattern fabrication by alkaline surface treatment, J. Vac. Sci. Technol. B., 1989, 1076–79, vol. 7(5).
Uchino, Shou–ichi et al., Synthesis of new metal–free diazonium salts and their applications to microlithigraphy, Journal of Photopolymer Science and Technology (1989); 2(1): 255–299.
Reiser, et al., Photoreactive Polymers: the Science and technology of Resists, 1989, 228–29.
Salamy, et al., Proc. Electrochem. Soc. 1989, 90:36.
Durand, et al., Nucleic Acids Res., 1990, 6353–59, vol. 18., No. 21.
Toshihiko Tanaka, et al., Sub–Halfmicron Lithography Using a High–Contrast–Line CEL, Japanese J. Applied Physics, Sep. 1990, 1880–61, vol. 29, No. 1.
R. Rforr, et al., Contrast enhancement of the resist latent image using exposure induced absorption amplification – fundamental, modeling, and applicability, Microelectronic Engineering, 1992, 321–328, vol. 17.
David M. Teegarden, et al., Contrast Enhancement Lithography System Based on Pyrylium Dye Bleach Chemistry, J. Imaging Science and Technology, 1993, 149–155, vol. 37, No. 2.
Thompson, L.F., et al., Introduction to Microlithography, America Chemical Society, 1994 212–232.
Huang, Proc. SPIE –Int. Soc. Opt. Eng., 1999, 3678, (Pt. 2) 340–51.

* cited by examiner

*Primary Examiner*—Bennett Celsa
(74) *Attorney, Agent, or Firm*—Thomas E. Malone; Philip L. McGarrig (57) ABSTRACT

Radiation-activated catalysts (RACs), autocatalytic reactions, and protective groups are employed to achieve a highly sensitive, high resolution, radiation directed combinatorial synthesis of pattern arrays of diverse polymers. When irradiated, RACs produce catalysts that can react with enhancers, such as those involved in autocatalytic reactions. The autocatalytic reactions produce at least one product that removes protecting groups from synthesis intermediates. This invention has a wide variety of applications and is particularly useful for the solid phase combinatorial synthesis of polymers.

6 Claims, 7 Drawing Sheets

METHODS OF ARRAY SYNTHESIS

STATEMENT OF RELATED APPLICATIONS

This application claims priority to U.S. Provisional Patent Application Ser. No. 60/223,290, filed Aug. 3, 2000, incorporated herein by reference in its entirety.

BACKGROUND OF THE INVENTION

Embodiments of the present invention relate to spatially defined chemical synthesis involving lithographic processes. In particular, embodiments of the present invention are directed to novel methods and compositions for synthesizing arrays of diverse polymer sequences, such as polypeptides and polynucleotides. According to a specific aspect of the invention, a method of synthesizing diverse polymer sequences, such as peptides or polynucleotides, is provided. The diverse polymer sequences are useful, for example, in nucleic acid analysis, gene expression monitoring, receptor and nucleic acid binding studies, surface based DNA computation, and integrated electronic circuits and other miniature device fabrication.

SUMMARY OF THE INVENTION

Improved methods of forming high-density arrays of peptides, polynucleotides, and other polymer sequences in a short period of time have been devised using combinatorial solid phase synthesis. See Kozal et al., *Nature Medicine*, Vol. 2, pp. 753–759 (1996), incorporated herein by reference in its entirety for all purposes. See also Pirrung et al., U.S. Pat. No. 5,143,854 (see also PCT Publication No. WO 90/15070), Fodor et al., PCT Publication No. WO 92/10092, and PCT Publication No. WO 95/11995; Fodor et al., *Science* (1991) 251:767–777, all incorporated herein by reference in their entirety for all purposes. Known methods of synthesizing high-density arrays employ radiation-labile protecting groups and photolithographic masks to achieve spatially defined combinatorial polymer synthesis on a substrate surface. In those embodiments, masks are used to control the selective exposure to radiation in specific locations of a surface provided with linker molecules containing radiation-labile or chemically labile protecting groups. In the exposed locations, the radiation-labile or chemical-labile protecting groups are removed. The surface is then contacted with a solution containing a desired monomer. The monomer has at least one site that is reactive with the newly exposed reactive moiety on the linker and at least a second reactive site protected by one or more radiation-labile or chemically labile protecting groups. The desired monomer is then coupled to the unprotected linker molecules. The process can be repeated to synthesize a large number of polymer sequences in specific locations.

Other methods for synthesizing high-density polymer arrays employ blocks containing channels for reagent delivery at preselected sites on the substrate. See U.S. Pat. No. 6,040,193, incorporated herein by reference for all purposes. In certain embodiments, a block is contacted with the substrate and the reagents necessary to form a portion of the immobilized polymer are permitted to access the substrate via the channel(s). The block or substrate can be rotated and the process repeated to form arrays of polymers on the substrate. The block channel method can be combined with light-directed methodologies.

Certain embodiments of the present invention provide novel methods, compositions, and devices useful in synthesizing novel high-density arrays of diverse polymer sequences. The polymer sequences are fashioned from individual synthesis intermediates and include diverse naturally or non-naturally occurring peptides, nucleotides, polypeptides or polynucleotides.

The presently claimed invention provides methods for more precisely controlling the removal of the protecting groups thus allowing for increased specificity in the removal of protecting groups. Generally, the presently claimed invention provides methods for introducing latency into the photochemical reaction, thus allowing for more precise removal of protecting groups at specific, known locations. In a first embodiment, a sequential multi-photon process is used to achieve latency in the photodeprotection process. In a first example of this embodiment, the invention provides for the addition of a layer of contrast enhancement material (CEM) to absorb stray light in unexposed areas to prevent removal of protecting groups in undesired locations. In a second example, the invention provides for a bleachable layer which actively quenches the excited states of the photodeprotecting groups. Additionally, a layer of CEM added to absorb stray light in unexposed areas could be bleached. Once the CEM is bleached the photo labile protecting groups can be removed. The CEM then competes with the photoprotecting groups for absorbing light. In a third example, the photodeprotecting groups themselves are modified such that multiple photons must be absorbed before the protecting group is removed.

U.S. Pat. No. 6,083,697, which is hereby incorporated by reference in its entirety for all purposes, discloses a novel chemical amplification process using a catalyst system which is initiated by radiation to assist in the synthesis of the polymer sequences as well as the use of photosensitive compounds which act as catalysts to chemically alter the synthesis intermediates in a manner to promote formation of polymer sequences. Such photosensitive compounds include what are generally referred to as radiation-activated catalysts (RACs), and more specifically photo activated catalysts (PACs). The RACs can by themselves chemically alter the synthesis intermediate or they can activate an autocatalytic compound which chemically alters the synthesis intermediate in a manner to allow the synthesis intermediate to chemically combine with a later added synthesis intermediate or other compound.

Using the techniques disclosed in the '697 patent, it is possible to advantageously irradiate relatively small and precisely known locations on the surface of the substrate. The radiation does not directly cause the removal of the protective groups, such as through a photochemical reaction upon absorption of the radiation by the synthesis intermediate or linker molecule itself, but rather the radiation acts as a signal to initiate a chemical catalytic reaction which removes the protective group in an amplified manner. Therefore, the radiation intensity as used in the practice of the present invention to initiate the catalytic removal by a catalyst system of protecting groups can be much lower than, for example, direct photo removal, which can result in better resolution when compared to many non-amplified techniques.

In a second embodiment of the presently claimed invention, latency is introduced by the addition of a compound (a catalyst scavenger) which competes for a catalyst which is capable of initiating a chemical catalytic reaction as described above. As one example, the presently claimed invention provides for the addition of an acid scavenger during the photochemical reaction to absorb stray acids which may catalyze removal of the protecting groups in undesired locations.

The present invention is advantageous because it makes possible the synthesis of polymers of any desired chemical sequence at known locations on a substrate with high synthesis fidelity, small synthesis features, and improved manufacturability. Embodiments of the present invention are useful in fabricating high-density nucleic acid probe arrays or immobilizing nucleic acid sequences on a surface of a substrate. High-density nucleic acid probe arrays provide an efficient means to analyze nucleic acids, to monitor gene expression and to perform computation.

One embodiment of the present invention provides methods of manufacturing high-density polymer arrays using chemical amplification techniques. The present invention also provides methods of manufacturing polymer arrays using less time and lower radiation intensities to improve polymer purity, to improve the spatial resolution and contrast between polymer and substrate and to decrease the area on the substrate where polymer sequences can be synthesized allowing many and different polymer sequences on the same substrate. The present invention also improves precision, contrast, and ease of manufacture in the production of polymer arrays.

These and other advantages of the present invention will become apparent by reference to the remaining portions of the specification and the attached drawings.

BRIEF DESCRIPTION OF THE DRAWINGS

In the course of the detailed description of certain preferred embodiments to follow, reference will be made to the attached drawings, in which.

DETAILED DESCRIPTION OF CERTAIN PREFERRED EMBODIMENTS

The present invention relies on many patents, applications and other references for details known to those of the art. Therefore, when a patent, application, or other reference is cited or repeated below, it should be understood that it is incorporated by reference in its entirety for all purposes as well as for the proposition that is recited.

As used in the specification and claims, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Additional methods and techniques applicable to array synthesis have been described in U.S. Pat. Nos. 5,143,854, 5,242,974, 5,252,743, 5,324,633, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,578,832, 5,593,839, 5,599,695, 5,624,711, 5,631,734, 5,677,195, 5,744,101, 5,744,305, 5,770,456, 5,795,716, 5,800,992, 5,831,070, 5,837,832, 5,856,101, 5,871,928, 5,858,659, 5,936,324, 5,968,740, 5,974,164, 5,981,185, 5,981,956, 6,025,601, 6,033,860, 6,040,138, and 6,090,555, which are all incorporated herein by reference in their entirety for all purposes.

As used herein, the following terms are intended to have the following general meanings:

1. Ligand:

A ligand is a molecule that is recognized by a receptor. Examples of ligand that can be investigated by this invention include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, and proteins.

2. Monomer:

A monomer is a member of the set of small molecules which are or can be joined together to form a polymer or a compound composed of two or more members. The set of monomers includes but is not restricted to, for example, the set of common L-amino acids, the set of D-amino acids, the set of synthetic and/or natural amino acids, the set of nucleotides, and the set of pentoses and hexoses, each set of which is readily known to those of skill in the art. The particular ordering of monomers within a polymer is referred to herein as the "sequence" of the polymer. As used herein, "monomers" refers to any member of a basis set for synthesis of a polymer, and is not limited to a single "mer". For example, dimers of the 20 naturally occurring L-amino acids form a basis set of 400 monomers for synthesis of polypeptides. Monomers can also include trimers, oligomers, polymers and so forth. Different basis sets of monomers may be used at successive steps in the synthesis of a polymer. Furthermore, each of the sets may include protected members, which are modified after synthesis. The invention is described herein primarily with regard to the preparation of molecules containing sequences of monomers such as nucleic acids, but could readily be applied in the preparation of other polymers. Such polymers include, for example, both linear and cyclic polymers of nucleic acids, polysaccharides, phospholipids, and peptides having either α-, β-, or γ-amino acids, heteropolymers in which a known drug is covalently bound to any of the above, polynucleotides, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Such polymers are "diverse" when polymers having different monomer sequences are formed at different predefined regions of a substrate. Methods of cyclization and polymer reversal of polymers are disclosed in co-pending application Ser. No. 796,727, filed Nov. 22, 1991, entitled "POLYMER REVERSAL ON SOLID SURFACES," incorporated herein by reference for all purposes.

3. Peptide: A peptide is a polymer in which the monomers are α-amino acids and are joined together through amide bonds, alternatively referred to as a polypeptide. Amino acids may be the L-optical isomer or the D-optical isomer. The term "polypeptide" as used herein refers to two or more amino acid monomers in length or greater and often includes more than 20 amino acid monomers or monomers on the order of hundreds. Standard abbreviations for amino acids are used (e.g., P for proline). Identification of amino acids and their abbreviations are well-known and are included in Stryer, Biochemistry, Third Ed., 1988, which is incorporated herein by reference for all purposes.

4. Receptor:

A receptor is a molecule that has an affinity for a ligand. Receptors may be naturally occurring or man-made molecules. They can be employed in their unaltered state or as aggregates with other species. Receptors may be attached, covalently or non-covalently, to a binding member, either directly or via a specific binding substance. Examples of receptors which can be employed by this invention include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, and organelles. Receptors are sometimes referred to in the art as antiligands. As the term receptors is used herein, no difference in meaning is intended. A "Ligand Receptor Pair" is formed when two molecules have combined through molecular recognition to form a complex. Specific examples of receptors which can be investigated by this invention include but are not restricted to:

a.) Microorganism Receptors: The determination of ligands that bind to microorganism receptors such as specific transport proteins or enzymes essential to survival of microorganisms would be a useful tool for discovering new classes of antibiotics. Of particular value would be antibiotics against opportunistic fungi, protozoa, and bacteria resistant to antibiotics in current use.

b.) Enzymes: For instance, a receptor can comprise a binding site of an enzyme such as an enzyme responsible for cleaving a neurotransmitter; determination of ligands for this type of receptor to modulate the action of an enzyme that cleaves a neurotransmitter is useful in developing drugs that can be used in the treatment of disorders of neurotransmission.

c.) Antibodies: For instance, the invention may be useful in investigating a receptor that comprises a ligand-binding site on an antibody molecule which combines with an epitope of an antigen of interest; analyzing a sequence that mimics an antigenic epitope may lead to the development of vaccines in which the immunogen is based on one or more of such sequences or lead to the development of related diagnostic agents or compounds useful in therapeutic treatments such as for autoimmune diseases (e.g., by blocking the binding of the "self" antibodies).

d.) Nucleic Acids: Sequences of nucleic acids may be synthesized to establish sequences recognized by various receptor molecules, such as protein or other DNA or RNA molecules. Nucleic acids within the scope of the present invention include naturally occurring or synthetic nucleic acids, nucleic acid analogs, modified nucleic acids, nucleic acids containing modified nucleotides, modified nucleic acid analogs, peptide nucleic acids and the like or mixtures thereof.

e.) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are discussed in, for example, PCT Publication No. WO 90/05746, WO 90/05749, and WO 90/05785, which are incorporated herein by reference for all purposes.

f.) Hormone Receptors: Determination of the ligand which binds with high affinity to a receptor such as the receptors for insulin and growth hormone is useful in the development of, for example, an oral replacement of the daily injections which diabetics must take to relieve the symptoms of diabetes or a replacement for growth hormone. Other examples of hormone receptors include the vaso-constrictive hormone receptors; determination of ligands for these receptors may lead to the development of drugs to control blood pressure.

g.) Opiate Receptors: Determination of ligands which bind to the opiate receptors in the brain is useful in the development of less-addictive replacements for morphine and related drugs.

5. Substrate: A material having a rigid or semi-rigid surface usually made from glass or suitable polymer materials. In many embodiments, at least one surface of the substrate will be substantially flat, although in some embodiments it may be desirable to physically separate synthesis regions for different polymers with, for example, wells, raised regions, etched trenches, or the like. In some embodiments, the substrate itself contains wells, trenches, flow through regions, etc. which form all or part of the synthesis regions. See also U.S. patent application Ser. No. 09/545,207, filed Apr. 7, 2000, which is hereby incorporated herein by reference in its entirety. According to other embodiments, small beads may be provided on the surface, and compounds synthesized thereon optionally may be released upon completion of the synthesis. Substrates are well known in the art and are readily commercially available through vendors such as USPG, PPG Industries, AFG Industries and others.

6. Protective Group: A material which may be selectively removed to expose an active site such as, in the specific example of an amino acid, an amine group. By way of illustration, protecting groups include but are not limited to those that are photolabile, acid labile, and base labile as described in U.S. Pat. Nos. 5,489,678, 5,753,788, 5,889,165, 6,083,697, and 6,147,205, all of which are incorporated herein by reference in their entirety for all purposes. For an extensive listing of protective groups useful in the practice of the present invention, see also Greene, T. W. and Wuts, P. G. M., Protective Groups in Organic Synthesis, (1991), incorporated herein by reference in its entirety for all purposes. Useful representative acid sensitive protective groups include dimethoxytrityl (DMT), tert-butylcarbamate (tBoc)

and trifluoroacetyl (Tfa). Useful representative base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester and the like.

7. Predefined Region: A predefined region is a localized area on a substrate. In a particularly preferred embodiment it is intended to be used for formation of a selected polymer. It is otherwise referred to herein in the alternative as "reaction" region, a "selected" region, or simply a "region." The predefined region may have any convenient shape, e.g., circular, rectangular, elliptical, wedge-shaped, etc. In some embodiments, a predefined region and, therefore, the area upon which each distinct polymer sequence is synthesized is smaller than about 1 $mm^2$, more preferably less than 1 $cm^2$, and still more preferably less than 0.5 $mm^2$. In most preferred embodiments, the regions have an area less than about 10,000 $\mu m^2$ or, more preferably, less than 100 $\mu m^2$. Within these regions, the polymer synthesized therein is preferably synthesized in a substantially pure form.

8. Substantially Pure: A polymer is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the polymer is at least 5% pure, more preferably more than 10% to 20% pure, more preferably more than 95% pure, where purity for this purpose refers to the ratio of the number of polymer molecules formed in a predefined region having a desired sequence to the total number of molecules formed in the predefined region.

9. Catalyst: A catalyst is any material that is not consumed in a chemical reaction and that affects the rate of the reaction. Reactions that are affected by catalysts are termed catalytic reactions. Autocatalytic reactions are reactions in which at least one of the products is also a catalyst for the reaction. An autocatalyst is a material that undergoes a reaction that produces a product that is also a catalyst for that same reaction. Some autocatalytic reactions have a relatively slow rate of reaction at the initial stage but the reaction is accelerated as it proceeds as more catalytic product is accumulated. Where a substance or a combination of substances undergoes two or more simultaneous reactions that yield different products, the distribution of products could be influenced by the use of a catalyst that selectively accelerates one reaction relative to the other(s).

10. Radiation-Activated Catalyst (RAC): A radiation activated catalyst (RAC) is a compound or group which produces at least one catalyst when exposed to radiation. RACs include but are not limited to radicals, acids, bases, ions, and metals.

11. Enhancer: An enhancer is any material that amplifies a radiation-initiated chemical signal so as to increase the effective quantum yield of the radiation. Enhancers include but are not limited to catalytic materials. The use of an enhancer in radiation-assisted chemical processes is termed chemical amplification. Chemical amplification has many benefits. Non limiting examples of the benefits of chemical amplification include the ability to decrease the time and intensity of irradiation required to cause a desired chemical reaction. Chemical amplification also improves the spatial resolution and contrast in patterned arrays formed using this technique.

12. Radiation Sensitizer: A radiation sensitizer is any material that shifts the wavelengths of radiation required to initiate a desired reaction. A sensitizer produces triplet states, effects energy absorption and energy transfer within molecules. A sensitizer also absorbs energy and then transfers energy to the molecule of interest so it shifts the wavelength and/or facilitates energy transfer.

13. Latency: When latency is introduced the response to radiation is delayed. In the case of a photoacid generator molecule latency can be introduced by an acid scavenger. The catalytic amount of acid generated produces a reaction cascade of acid generation. Under some conditions it is necessary to accumulate a certain amount of acid in the system before complete removal of the acid labile protecting group is realized. The introduction of an acid scavenger to the system can be used to slow the removal of the protecting group by requiring a greater amount of acid to accumulate.

Photobleachable compounds can also be used to introduce latency. For example, when a CEM comprised of a photobleachable material is used in combination with a compound such as MeNPOC photodeprotection can be slowed. In the absence of such a compound, direct photolysis of photolabile compounds such as MeNPOC exhibits linear responses to light such that photodeprotection rates are proportional to the amount of light absorbed. In the presence of a CEM comprised of a photobleachable compound, the CEM competes with the MeNPOC for the absorbancy of light. It is only after the opaque CEM has absorbed light and converted to a transparent film that the MeNPOC can then react. MeNPOC therefore lies dormant until all the CEM is bleached.

A number of patents, patent applications, publications and other references are cited throughout the disclosure. Unless otherwise specified, each of these cited references is incorporated by reference in their entirety for all purposes.

General

The techniques of the present invention are useful in many fields, particularly in nucleic acid analysis, gene expression monitoring, amplification of nucleic acids, drug discovery, fabrication of miniature electronic, mechanic or other devices, and DNA based computation. The present invention provides methods, devices, and compositions for the formation of arrays of large numbers of different polymer sequences. The methods and compositions provided herein involve the conversion of radiation signals into chemical products in an amplified manner that is particularly useful in polymer synthesis. The invention also includes the arrays formed using the methods and compositions disclosed herein. One aspect of the invention includes methods, compositions, and devices for the synthesis of an array of different polymers in selected and predefined regions of a substrate. Another aspect of the invention includes those arrays and various methods of using them.

Such arrays are used in, for example, nucleic acid analysis. Polynucleotide or nucleic acid arrays are especially suitable for checking the accuracy of previously elucidated sequences and for detecting mutations and polymorphisms. Such arrays are also used in screening studies to evaluate their interaction with receptors such as antibodies and nucleic acids. For example, certain embodiments of the invention provide for the screening of peptides to determine which, if any, of a diverse set of peptides has strong binding affinity with a receptor.

In some embodiments, the arrays formed by the present invention are used in competitive assays or other well-known techniques to screen for compounds having certain activities. For example, vast collections of synthetic or natural compounds are immobilized on predefined regions of a substrate. The reaction of the immobilized compounds (or compound) with various test compositions such as the members of a chemical library or a biological extract are tested by dispensing small aliquots of each member of the library or extract to a different region. In one embodiment, a large collection of human receptors is deposited on a substrate, one in each region to form an array. A plant or animal extract is then screened for binding to various receptors of the array.

In a preferred embodiment using microarray technology on a substrate, nucleic acids or other polymers with different sequences can be immobilized, each in a predefined area on a surface. In some embodiments, such immobilized nucleic acid arrays are used in hybridization assays for gene expression monitoring, nucleic acid amplifications, nucleic acid computation, and nucleic acid analysis in general. For example, 10, 50, 60, 100, $10^3$, $10^4$, $10^5$, $10^6$, $10^7$, or $10^8$ different monomer sequences may be provided on the substrate. The nucleic acids of a particular sequence are provided within a predefined region of a substrate, having a surface area, for example, of about 1 cm$^2$ to $10^{-10}$ cm$^2$. In some embodiments, the regions have areas of less than about $10^{-1}$, $10^{-2}$, $10^{-3}$, $10^{-4}$, $10^{-5}$, $10^{-6}$, $10^{-7}$, $10^{-8}$, $10^{-9}$, or $10^{-10}$ cm$^2$. For example, in one embodiment, there is provided a planar, non-porous support having at least a first surface, and a plurality of different nucleic acids attached to the first surface at a density exceeding about 400 different nucleic acids/cm$^2$, wherein each of the different nucleic acids is attached to the surface of the solid support in a different predefined region, has a different determinable sequence, and is, for example, at least 4 nucleotides in length. The nucleic acids may be, for example, about 4 to 60 nucleotides in length. The number of different nucleic acids may be, for example, 1000 or more. Further discussion on arrays of nucleic acids or other polymers immobilized on a surface are described in detail in U.S. Pat. No. 5,744,305, the disclosure of which is incorporated herein.

In a preferred embodiment, the presently claimed invention employs the radiation directed methods discussed in U.S. Pat. Nos. 5,143,854 and 6,083,697, previously incorporated herein by reference. The radiation-directed methods discussed in that patent involve activating predefined regions of the substrate and then contacting the substrate with a preselected monomer solution. The predefined regions can be activated with, for example, a light source shown through a mask (much in the manner of photolithographic techniques used in integrated circuit fabrication). Other regions of the substrate remain inactive because they are blocked by the mask from illumination. Thus, a light pattern defines which regions of the substrate react with a given monomer. By repeatedly activating different sets of predefined regions and providing different monomer compositions thereto, a diverse array of polymers is produced on or near the substrate. Other regions of the substrate remain inactive because they are blocked by the mask from illumination and remain chemically protected. Thus, a light pattern defines which regions of the substrate react with a given monomer. Of course, other steps such as washing unreacted monomer solution from the substrate can be used as necessary.

In some preferred embodiments of the present invention, a sequential multi-photon process is used to achieve latency in the photodeprotection process. In a first example of this embodiment, the invention provides for the addition of contrast enhancement material (CEM) to produce a contrast enhancement layer (CEL) which is capable of absorbing stray light in unexposed areas.

Stray light may lead to removal of protecting groups in undesired locations. In a second example, the invention provides for a bleachable layer that competes with the photoprotecting groups for energy absorption in which the photoactive molecules must first become bleached or consumed before allowing radiation to reach the photolabile protecting groups of interest. In a third example, the photodeprotecting groups themselves are modified such that multiple photons must be absorbed before the protecting group is removed.

In some preferred embodiments of the present invention, a substrate with a linker having a protective group is provided with a radiation-activated catalyst (RAC), an enhancer, and a catalyst scavenger. The RAC is selectively irradiated to generate a catalyst in preselected regions. The catalyst and the enhancer assist the removal of the protective groups on the linker. The catalyst scavenger precisely controls the removal of the protective groups on the linker. As the concentration of catalyst scavenger is increased, the area and amount of protective groups removed is decreased. The linker, having a newly exposed reactive group, is contacted with a monomer capable of reacting with the linker. The monomer also has a protective group that can be removed in a subsequent reaction step. In this stepwise manner, diverse arrays of polymers are synthesized at preselected regions of a substrate.

Light Directed Synthesis

According to one embodiment, the presently claimed invention employs the radiation directed methods discussed in U.S. Pat. Nos. 5,143,854 and 6,083,697, previously incorporated herein by reference. In the radiation-directed methods described in the '854 patent, the surface of a solid support, optionally modified with spacers having photolabile protecting groups such as NVOC or MeNPOC, is illuminated through a photolithographic mask, yielding reactive groups (typically hydroxyl groups) in the illuminated regions. A 3'-O-phosphoramidite activated deoxynucleoside (protected at the 5'-hydroxyl with a photolabile protecting group) is then presented to the surface and chemical coupling occurs at sites that were exposed to light. Following capping, and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of oligonucleotides is produced. Alternatively, an oligomer of from, for example, 4 to 30 nucleotides can be added to each of the preselected regions rather than synthesizing each member in a monomer by monomer approach. At this point in the synthesis, either a flexible linking group or a probe can be attached in a similar manner. For example, a flexible linking group such as polyethylene glycol will typically have an activating group (i.e., a phosphoramidite) on one end and a photolabile protecting group attached to the other end. Suitably derivatized polyethylene glycol linking groups can be prepared by the methods described in Durand, et al. Nucleic Acids Res. 18:6353–6359 (1990). Briefly, a polyethylene glycol (i.e., hexaethylene glycol) can be mono-protected using MeNPOC-chloride. Following purification of the mono-protected glycol, the remaining hydroxy moiety can be activated with 2-cyanoethyl-N,N-diisopropylaminochlorophosphite. Once the flexible linking group has been attached to the first oligonucleotide, deprotection and coupling cycles will proceed using 5'-protected, 3'-O-phosphoramidite activated deoxynucleosides or intact oligomers. Deprotection and coupling cycles can also proceed using 3'-protected, 5'-O-phosphoramidite activated nucleosides, deoxynucleosides, or ribonucleosides. Probes can be attached in a manner similar to that used for the flexible linking group. When the desired probe is itself an oligomer, it can be formed either in stepwise fashion on the immobilized oligonucleotide or it can be separately synthesized and coupled to the immobilized oligomer in a single step. For example, preparation of conformationally restricted beta-turn mimetics will typically involve synthesis of an oligonucleotide as described above, in which case the last nucleoside monomer will be derivatized with an aminoalkyl-functionalized phosphoramidite. See, U.S. Pat. No. 5,288,514, previously incorporated by reference. The desired peptide probe is typically formed in the direction from carboxyl to amine terminus. Subsequent coupling of a 3'-succinylated nucleoside, for example, provides the first monomer in the construction of the complementary oligonucleotide strand (which is carried out by the above methods). Alternatively, a library of probes can be prepared by first derivatizing a solid support with multiple poly(A) or poly(T) oligonucleotides which are suitably protected with photolabile protecting groups, deprotecting at known sites and constructing the probe at those sites, then coupling the complementary poly(T) or poly(A) oligonucleotide.

Resist Embodiments

According to one embodiment of the presently claimed invention, spatially defined polymer synthesis will be performed by depositing a photoresist such as those used extensively in the semiconductor industry, more fully discussed in Ghandi, "VLSI Fabrication Principles," Wiley (1983) Chapter 10, incorporated herein by reference in its entirety for all purposes. According to these embodiments, a resist is deposited, selectively exposed and etched, leaving a portion of the substrate available for coupling. These steps of depositing resist, selectively removing resist and monomer coupling are repeated to form polymers of desired sequence at desired locations.

In some specific embodiments, a positive-tone resist comprised of diazonapthoquinone-novolac (DNQ/N) is incorporated in a cresol-formaldehyde polymer matrix. This resist and its variants are used routinely in the microelectronics industry for submicron resolution lithography, as more fully discussed in Reiser, "Photoreactive Polymers: the Science and Technology of Resists", Wiley (1989), incorporated herein by reference in its entirety for all purposes. High contrast detritylation at a resolution of <4 microns has been demonstrated in simple contact printing experiments with this resist. Unfortunately, the alkaline conditions needed to develop the DNQ/N resists (aqueous [OH$^-$]>0.1 M) complicates its direct use in a multi-step polymer synthesis, such as the polynucleotide array fabrication process, because of the hydrolysis of akali-labile nucleobase protecting groups that are used to prevent side reactions during synthesis with standard phosphoramidite monomers using dimethoxytrityl (DMT) as a protecting group. A preferred embodiment uses alkali-resistant acid labile nucleobase protecting groups, such as monomethoxytrityl (MMT), and akali-labile 5' hydroxyl groups to avoid this difficulty. MMT is completely resistant to the aqueous alkali developer, and readily removed with diluted acid post-synthesis. Alkali labile protection is used for the 5' hydroxyl group so that it will be susceptible to cleavage in the same alkaline solutions used for resist development, allowing the two processes to occur simultaneously. One preferred embodiment uses a benzyol group as an alkali-labile protection group because the benzyol group is sufficiently selective for the 5' hydroxyl group in preparing the monomer. More sterically hindered acyl protecting moieties, such as isobutyrl or pivaloyl, can also be used to enhance selectivity in monomer preparation. See also U.S. Pat. No. 6,147,205, which is hereby incorporated by reference in its entirety for all purposes.

Contrast Enhancement Layer

The use of contrast enhancement layers (CELs) in the semiconductor industry has been well described. In the semiconductor industry, these layers are applied to the substrate surface on top of the photoresist layer to reduce light diffraction and improve topographical sharpness. See, e.g. Griffing and West IEEE Electron Device Letters EDL-4(1): 14(1983). The CEL is a photobleachable thin film which is opaque prior to exposure to radiation but upon radiation exposure becomes optically transparent in those regions of highest radiation intensity. The CEL acts to absorb stray light in the unexposed areas, thus allowing for more specific definition between exposed and unexposed regions of the substrate.

Compounds that are useful as CEMs include, for example, dye molecules that absorb at the exposure wavelength and after photoconversion or photobleaching produce products that are transparent at the exposure wavelength enabling the underlayer photoresist to be exposed in a non-linear process. A number of compounds suitable for CELs have been described and include, for example, nitrones, polysilanes, diazonium salts, diazo analogs, alkalines such as tetramethylammonium hydroxide (TMAH), "D6", pyrylium dyes, and "built-on-mask" (BOM) material. (See, for example, Thompson, L. F.; Willson, C. G.; and Bowden, M. J., Introduction to Microlithography; *American Chemical Society*, 1994, incorporated herein by reference in its entirety for all purposes.) The use of polysilanes as a resist material for CEL is described in Hofer et al., "Contrast enhanced uv lithography with polysilanes" SPIE Vol. 469 Advances in Resist Technology 108–116 (1984), and West et al., "Contrast Enhanced Photolithography: Application of Photobleaching Processes in Microlithography" Journal of Imaging Science 30: 65–68 (1986). The use of diazonium salt chemistry is described in Halle, L., J. Vac. Sci. Technol. B., 1985, 3(1), 323 and Uchine et al. Proc. Poly. Mat. Sci. And Eng., 1986, 55, 604. The use of alkaline materials is described in Endo et al., "High-aspect-ratio resist pattern fabrication by alkaline surface treatment" J. Vac. Sci. Technol. B 7 (5) 1076–1079, (1989). The use of "D6" which is prepared from 4-N,N -dimethylaminobenzenediazoniumtrifluoromethanesulfonate and poly (B-vinyl-pyrrolidone is described in Tanaka et al., Japanese Journal of Applied Physics 29 (9) 1960–1861 (1990). The use of pyrylium dyes is described in J. Imaging Science and Technology 37 (2)

149–155 (1993). See also, Sheats et al., SPIE Proc. 1986, 631, 171 and U.S. Pat. No. 4,705,729.

The particular dye that is used may be determined by the wavelength at which it is desirable for the bleaching to take place. For example, it is desirable for the CEL dye to react to a wavelength similar to that at which the photoprotecting chemical or photoresist reacts. This allows the CEL to compete with the photoprotecting chemical or photoresist for the same photons, providing the sequential multi-photon process. Preferably, if the wavelength at which the photoprotecting chemical or photoresist reacts is at wavelength X, the dye should react at a wavelength of X±30 nm.

In a preferred embodiment, pyrylium dye is used as the dye in the CEL. Pyrylium salts are electron acceptors. Excitation of the dye by light results in a single electron transfer to the dye from a coreactant. A wide variety of electron donors may be used as the coreactant. A preferred coreactant is based on a solvent separated radical and radical cation pair to generate the product or regenerate the starting material. In a preferred embodiment the coreactant is an allyl thioureas. In an even more preferred embodiment the coreactant is triallyl thiourea (TATU), diallylthiourea (DATU) or 1-allyl-3-(2-hydrodxyethyl)-2-thiourea (HATU), with TATU being most preferred. The reactant:dye ratio can be modified to provide the desired latency effect. The polymeric reactant:dye ratios are preferably between 1:1 and 5:1, more preferably between 2:1 and 5:1, more preferably between 3.5:1 and 4.5:1 and most preferably 4:1.

In a further preferred embodiment, diazonium dye is used as the dye in the CEL. An advantage to using the diazonium dye is that no coreactant is needed.

The dye is solubilized in a polymeric binder to allow the dye to be coated on the desired substrate. Any known polymeric binder may be used. It may be desirable to avoid polymeric binders which are photosensitive, or which contain structures such as aromatic rings which may interfere with the synthesis chemistry. Preferred polymeric binders include poly(vinyl butyral) and poly(methyl methacrylate) in acetonitrile, however those of skill in the art will be familiar with a wide variety of polymeric binders which are suitable for the methods of the presently claimed invention. As demonstrated in the examples section, the percentage of dye in solution can be manipulated to provide the desired latency. The preferred percentage of dye in solution is dependent on the particular dye being used. However, in general the percentage of dye in solution is preferably between 1% and 10%, and more preferably between 2%–10%.

The CEL is typically applied by spin-coating the CEL onto the substrate to be coated. The thickness of the CEL can be controlled by the speed of rotation and the time of deposition. The spin speed is preferably between 500 rpm and 6000 rpm, more preferably between 1000 rpm and 4000 rpm, and most preferably between 1500 rpm and 2500 rpm. The spin time is preferably between 15 seconds and 2 minutes, preferably between 20 seconds and 1 minute and most preferably between 25 seconds and 45 seconds. The final film thickness is preferably between 0.1 microns and 1 microns, more preferably between 0.2 microns and 0.8 microns and most preferably between 0.4 microns and 0.6 microns.

However, as described below, for some methods of the presently claimed invention, it may be desirable or preferable to dip the substrate into the CEM. For example, the substrate may be dipped into a container holding a solution of CEM. When the dipping technique is used, the thickness of the CEL can be controlled by the speed with which the substrate is removed from the CEM. One advantage of the dipping method is that multiple substrates may be dipped at the same time. For example, a carrier containing a number of substrates may be dipped into the CEM solution.

According to one method of the presently claimed invention, resist chemistry is used in synthesis as described above. The CEL is applied on top of the resist layer. The old CEL is then stripped after the synthesis round and a new CEL may be reapplied before each round of synthesis, as desired.

According to another method of the presently claimed invention, rather than depositing the CEL on a photoresist layer, the CEL is deposited directly on the photoprotected substrate or polymer layer prior to each synthesis step. The CEL is first coated on the photoprotected substrate and may be reapplied between successive synthesis rounds as desired, thus depositing the CEL in a photoresist layer.

In another method of the presently claimed invention, the CEL may be deposited on a blank which is then inserted between the mask and the substrate between rounds of synthesis. An advantage of this method is that the steps of stripping a previous CEL and reapplying a new layer between each round of synthesis can be skipped. In this method, only the blank is subjected to stripping and reapplication. The CEL may be applied to the blank either by spin coating or by dipping as described above. Either the same blank can be recoated and reused for each synthesis round or, preferably, multiple coated blanks can be used.

In another method of the presently claimed invention, the CEL may be deposited directly on the mask. This reduces the number of substrates through which each photon must pass prior to reaching the photobleachable target, thus reducing potential deprotection errors due to undesired light refraction. If a different mask is used for each round of synthesis, all the masks can be dipped simultaneously in the CEM solution prior to synthesis.

Reagents, such as solvents, used in the processing of CEM may affect photo-speed, coating uniformity, thermal flow and adhesion. (See, for example, Salamy et al. Proc. Electorchem. Soc. 90:36 (1989)). If desired, the substrate may be baked after coating to drive off any solvents. Preferably baking temperatures are between 0 and 100° C. Baking time is preferably between 0 and 10 minutes.

Figure 1:
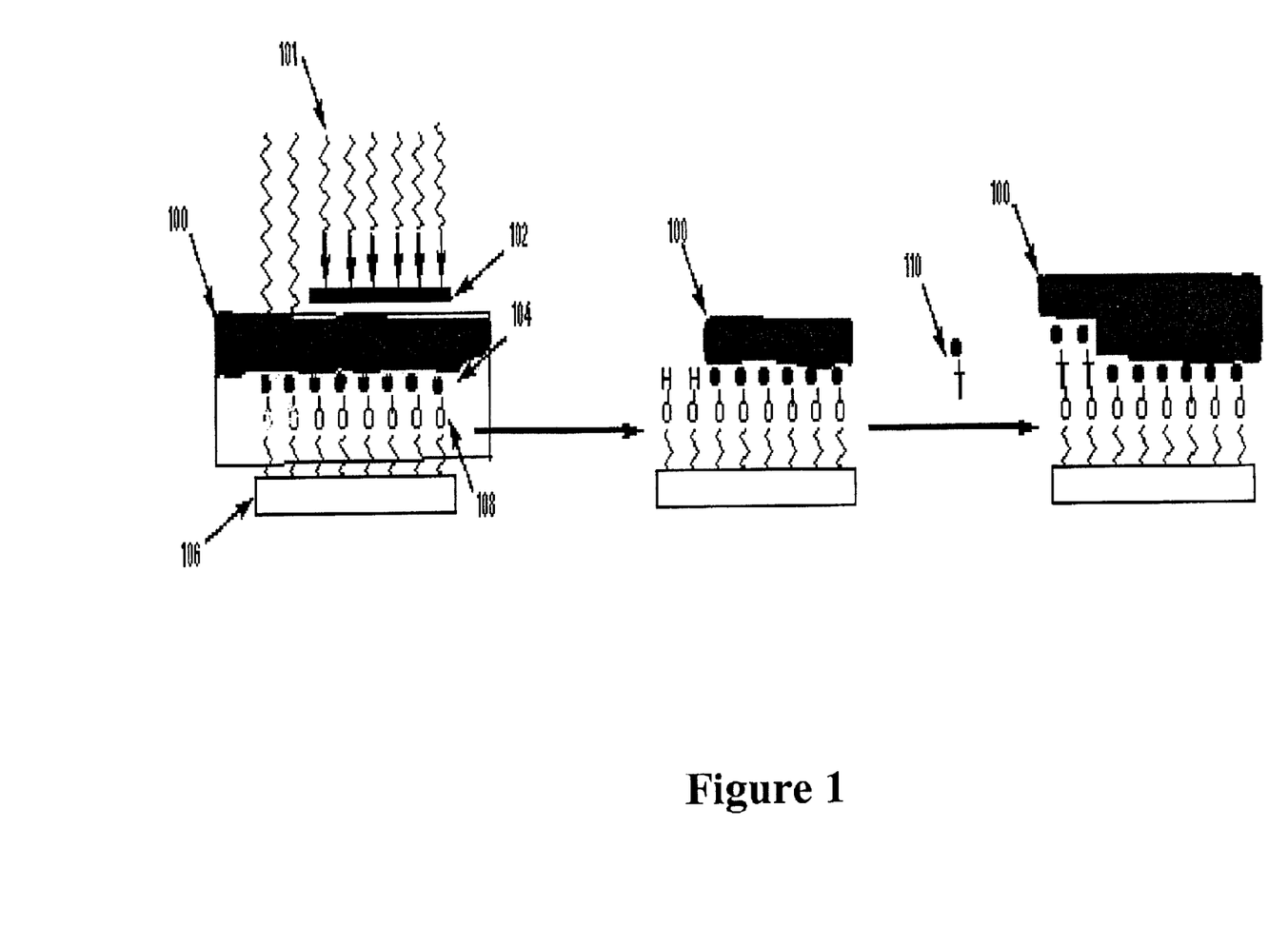
FIG. 1 is a schematic illustration of the fabrication of high density probe arrays using contrast enhancement materials.

FIG. 1 illustrates one example of the use of a CEL in the fabrication of high-density probe arrays. A glass substrate 106 comprising a synthesis intermediate to which are attached monomers and polymers 108 and protecting groups 104 is coated with a CEL 100 comprising a photobleachable dye. A mask 102 comprising light transmissive regions is placed over the substrate and the substrate is irradiated with light 101 through the mask. The dye bleaches in the direct high intensity photolysis region, but remains opaque to low intensity scattered light resulting from diffraction. Following exposure, the CEL is removed and a monomer 110 is coupled. The CEL is then reapplied and the process is repeated.

Figure 2:
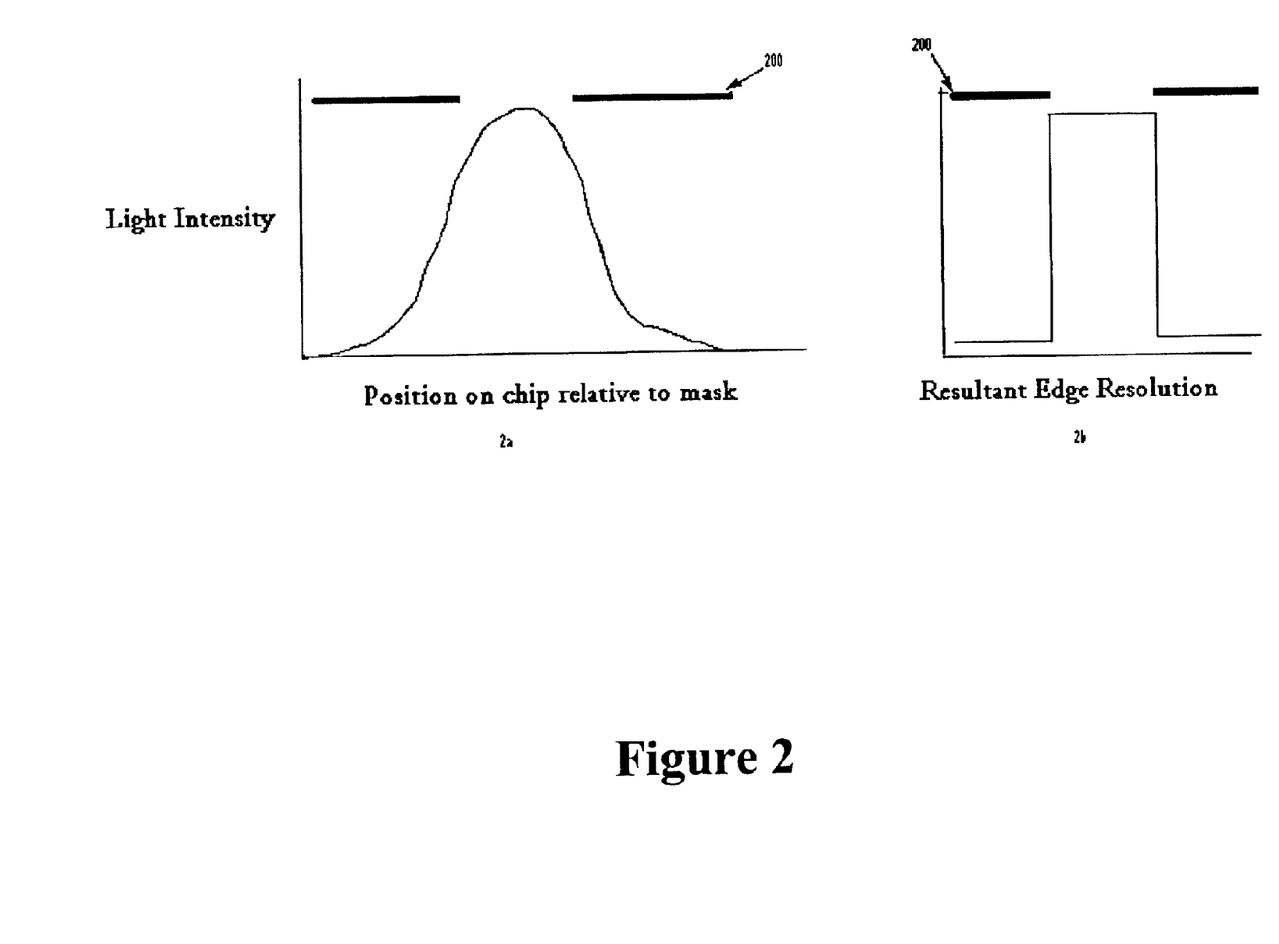
FIG. 2 is a schematic illustration of the distribution light intensity with and without contrast enhancement materials to improve edge resolution on photopatterned features

FIG. 2 depicts an illustration of the sharpening of the edge resolution as a result of the dye bleaching only in areas of direct high intensity light. FIG. 2a shows a graph of the light intensity versus the position on the chip relative to the mask 200, representing actual light that reaches the surface. FIG. 2b shows the sharp edge resolution that results from the nonlinear response of the CEM to the various light intensities produced, representing the actual photobleachable region as modulated by the CEM.

Bleachable Quenchers

In yet another embodiment, a layer of material is applied to the probe arrays surface that quenches the excited states of the photodeprotecting groups. The quenching molecules are chosen to degrade under exposure to radiation to produce a quenching-incompetent product. The quenching rate should be sufficiently fast to inhibit the undesired photochemistry. Once the quenching molecules are degraded, the protecting groups are exposed and available for deprotection by radiation.

Photochemical Precursor

In yet another embodiment, the photodeprotecting group itself is modified such that it must absorb a first photon to transform it to a form that can absorb a second photon which then removes the protecting group.

Photo Acid Generator (PAG) and Acid Scavenger

One embodiment of the present invention includes a photochemical amplification method wherein photon radiation signals are converted into chemical signals in a manner that increases the effective quantum yield of the photon in the desired reaction. The use of photochemical amplification in methods of synthesizing patterned arrays (PASPA) is particularly advantageous since the time and the intensity of irradiation required to remove protective groups is decreased relative to known direct photochemical methods. Additionally, photoacid generators (PAG) generate acid directly upon radiation to remove protecting groups.

In general, radiation signals are detected by a catalyst system including, for example, a photo activated catalyst (PAC). The catalyst activates an enhancer, which increases the effective quantum yield of the photons in subsequent chemical reactions. Such subsequent reactions include the removal of protective groups in the synthesis of patterned arrays. It is desirable to remove all the protecting groups in a very precise location without removing protecting groups outside of the desired location. To prevent removal of protective groups in undesirable locations, a catalyst scavenger in some cases may be added but is not necessary to compete for the catalyst, thus enabling the user to more specifically define the area effected by the radiation signals.

In certain embodiments, a photo activated acid catalyst (PAAC) is irradiated. The resulting acid produced from the PAAC activates an enhancer to undergo an acid-catalyzed reaction to itself produce an acid that removes acid labile protecting groups from a linker molecule or synthesis intermediate. The combination of PACs and enhancers converts and amplifies the photon signal irradiated on the surface of the substrate. Because of the amplification, the effective quantum yield of the radiation directed at the surface of the substrate is much larger than one, resulting in high sensitivity.

One way of controlling acid catalyst "bleed-over" is the addition of an acid scavenger which serves to soak up the acid catalyst in competition with the photo activation reaction. Adjusting the concentration of acid catalyst aids in fine tuning the area in which the protecting groups are removed.

According to one embodiment of the present invention, linker molecules having reactive functional groups protected by protecting groups are provided on the surface of a substrate. A catalyst system including a PAC and an enhancer are also provided on the surface. In some embodiments, an acid catalyst scavenger may also be added. A set of selected regions on the surface of the substrate is exposed to radiation using well-known lithographic methods discussed, for example, in Thompson, L. F.; Willson, C. G.; and Bowden, M. J., Introduction to Microlithography; American Chemical Society, 1994, pp. 212–232, incorporated herein by reference in its entirety for all purposes.

The PAC catalyst activated by the region-selective irradiation discussed above acts to initiate a reaction of the enhancer. The enhancer produces at least one product that removes the protecting groups from the linker molecules in the first selected regions. Preferably, the enhancer is capable of removing protective groups in a catalytic manner. In some cases an acid scavenger may be added to react with the acid catalyst, limiting the amount of acid catalyst available to react with the enhancer. The substrate is then washed or otherwise contacted with a first monomer that reacts with exposed functional groups on the linker molecules. Those bound monomers are termed first-bound monomers.

A second set of selected regions is, thereafter, exposed to radiation. The radiation-initiated reactions remove the protecting groups on molecules in the second set of selected regions, i.e. the linker molecules and the first-bound monomers. The substrate is then contacted with a second monomer containing a removable protective group for reaction with exposed functional groups. This process is repeated to selectively apply monomers until polymers of a desired length and desired chemical sequence are obtained. Protective groups are then optionally removed and the sequence is, thereafter, optionally capped. Side chain protective groups, if present, are also optionally removed.

In one preferred embodiment, the monomer is a 2'-deoxynucleoside phosphoramidite containing an acid removable protecting group at its 5' hydroxyl group. As stated previously, in an alternate embodiment, the protecting group is present at the 3' hydroxyl group if synthesis of the polynucleotide is from the 5' to 3' direction. The nucleoside phosphoramidite is represented by the following formula:

wherein the base is adenine, guanine. thymine, cytosine or any other nucleobase analog; $R_1$ is a protecting group which makes the 5' hydroxyl group unavailable for reaction and includes dimethoxytrityl, MeNPOC, tert-butyloxycarbonyl or any of the protecting groups previously identified; $R_2$ is cyanoethyl, methyl, t-butyl, trimethylsilyl and the like; $R_3$ and $R_4$ are isopropyl, cyclohexone and the like; and $R_5$ is hydrogen, NR'R", OR, SR, CRR'R", or OSi(R''')$_3$ wherein R, R', R", and R''' are hydrogen, alkyl and the like. Exocyclic amines present on the bases can also be protected with acyl protecting groups such as benzoyl, isobutyryl, phenoxyacetyl and the like. The linker molecule contains an acid- or base-removable protecting group. Useful linker molecules are well known to those skilled in the art and representative examples include oligo ethers such as hexaethylene glycol, oligomers of nucleotides, esters, carbonates, amides and the like. Useful protecting groups include those previously listed and others known to those skilled in the art.

In another preferred embodiment, the monomer is an amino acid containing an acid- or base-removable protecting group at its amino or carboxy terminus and the linker molecule terminates in an amino or carboxy acid group bearing an acid- or base removable protecting group. Protecting groups include tert-butyloxycarbonyl, 9-fluorenylmethyloxycarbonyl, and any of the protective groups previously mentioned and others known to those skilled in the art.

In a preferred embodiment the catalyst scavenger may be an acid scavenger such as an amine and more specifically may be trioctylamine or 2,5-di-tertbutylanaline. Other acid scavengers include carboxylate salts and hydroxides. See, e.g. Huang, Proc. SPIE-Int. Soc. Opt. Eng. (1999), 3678 (Pt. 2) 1040–1051. Those of skill in the art will be familiar with other acid scavengers which will be appropriate for the present invention.

In another preferred embodiment the catalyst scavenger may be a base scavenger such as acetic acid or trichloro acetic acid. Other base scavengers include phosphoric acid, sulfuric acid or any other carboxylic acid. Care should be taken to chose a base scavenger which will not interfere with or destroy the monomer. Those of skill in the art will be familiar with other base scavengers which will be appropriate for the present invention.

It is apparent to those skilled in the art that photochemically amplified radiation-based activation is not limited to photo activated enhancers or catalysts or to acid or base production cascades. Various compounds or groups can produce catalysts or enhancers in response to radiation exposure. Non-limiting examples include photogeneration of radicals using diphenylsulfide, benzoylperoxide, 2,2'-azobis(butyronitrile), benzoin and the like; cations such as triarylsulfonium salts, diaryl iodonium salts and the like; and anions. Furthermore, it is apparent to those of skill in the art that the catalyst scavengers are not limited to acid or base scavengers but may include any other compound which will interfere with the catalysts ability to interact with the enhancer.

In a preferred embodiment, the catalyst and catalyst scavenger are capable of engaging in a cyclic reaction. For example, a compound X comprises subcompound Y which is capable of acting as a catalyst and subcompound Z which is capable of acting as a catalyst scavenger. Compound X is capable of entering into an excited state after exposure to radiation. During this excited state the subcompounds Y and Z separate and subcompound Y is free to catalyze removal of protecting groups. In a further preferred embodiment, the subcompounds Y and Z are capable of remaining in this excited state for only a very short period of time. This time period may be from between a few nanoseconds to a few milliseconds. After the time period lapses, subcompounds Y and Z are free to interact with one another once again forming compound X Exposure to radiation may then initiate another cycle.

In a preferred embodiment, compound X is very stable prior to exposure to radiation, and only capable of interacting with other molecules during the excited state.

Radiation and Substrates

The selection of radiation sources is based upon the sensitivity spectrum of the compound to be irradiated. Potential damage to synthesis substrates, intermediates, or products is also considered. In some preferred embodiments, the radiation could be ultraviolet (UV), infrared (IR), or visible light. In a specific embodiment, the radiation source is a light beam with a wavelength in the range of from 190–500 nm, preferably from 250–450 nm, more preferably from 365–400 nm. Specific radiation wavelengths include 193 nm, 254 nm, 313 nm, 340 nm, 365 nm, 396 nm, 413 nm, 436 nm, and 500 nm. Suitable light sources include high pressure mercury arc lamps and are readily commercially available from Oriel, OAI, Cannon, A-B Manufacturing. In embodiments utilzing the catalytic system, the sensitivity spectrum of the RAC can be altered by providing radiation sensitizers. The energy of the sensitizer must be matched to the PAC and include 2-ethyl-9,10-dimethoxy-anthracene, perylene, phenothiazine, xanthone and the like. Many radiation sensitizers are known to those skilled in the art and include those previously mentioned. It is to be understood that one of ordinary skill in the art will be able to readily identify additional radiation sensitizers based upon the present disclosure.

In preferred embodiments, the substrate is conventional glass, pyrex, quartz, any one of a variety of polymeric materials, or the like. Of course, the substrate may be made from any one of a variety of materials such as silicon, polystyrene, polycarbonate, or the like. In operation, the surface of the substrate is appropriately treated by cleaning with, for example, organic solvents, methylene chloride, DMF, ethyl alcohol, or the like. Optionally, the substrate may be provided with appropriate linker molecules on the surface thereof. The linker molecules may be, for example, aryl acetylene, ethylene glycol oligomers containing from 2–10 monomers or more, diamines, diacids, amino acids, or combinations thereof. In some embodiments the surface may be silanated. Thereafter, the surface is provided with protected surface active groups such as tertbutyloxycarbonyl (TBOC) or fluorenylmethoxycarbonyl (FMOC) protected amino acids. Such techniques are well known to those of skill in the art.

A. Nucleic Acid Analysis

The present invention provides an efficient means for fabricating high-density polynucleotide arrays, which have been successfully employed in a variety of nucleic acid analysis applications. Polynucleotide arrays are useful in a variety of applications including but not limited to detecting specific mutations or polymorphisms and checking the accuracy and resolving ambiguity of previously elucidated sequences.

B. Gene Expression Monitoring

Polynucleotide arrays can be used for simultaneously monitoring the expression of multiple genes and eventually all genes as transcript sequences become available. Gene expression monitoring at the mRNA level can be carried out by extracting mRNA or total RNA from tissue or cell samples; fragmenting and labeling the RNA samples; hybridizing the fragmented RNA samples to polynucleotide arrays and detecting the hybridization pattern to determine quantitatively the level of specific mRNAs. Various levels of transcript processing, such as RNA splicing, can also be monitored using polynucleotide arrays. Specific embodiments for gene expression monitoring are disclosed in U.S. Pat. No. 6,040,138, and PCT Application No. PCT/US96/14839, filed Sep. 13, 1996, incorporated by reference herein in their entirety for all purposes.

The present invention is also used to immobilize nucleic acid sequences on a substrate. Immobilized nucleic acid sequences are used for various hybridization assays. Hybridization of such immobilized nucleic acids with mRNA samples (or immobilized mRNA samples) is detected to monitor gene expression in some embodiments.

C. Drug Discovery

The significantly enhanced resolution made possible by the present invention permits the synthesis of more polymers on a given surface area. Therefore, the invention can be used for building chemical libraries and screening for biological activities of a large number of compounds in drug discovery using combinatorial chemistry.

D. DNA Computation

Polynucleotides have been used in DNA based computation. Spatially defined polynucleotide arrays are useful for certain DNA computation tasks. DNA computation employs the ligation, enzymatic cleavage and hybridization of polynucleotides. In some embodiments, polynucleotide arrays are used for accessing the result of DNA computation by detecting the presence of specific polynucleotides by specific hybridization. In some other embodiments, DNA computation is accomplished by manipulating polynucleotide arrays fabricated with chemical amplification.

EXAMPLES

Reference will now be made in detail to illustrative embodiments of the invention. While the invention will be described in conjunction with the illustrative embodiments, it will be understood that the invention is not so limited. On the contrary, the invention is intended to cover alternatives, modifications and equivalents, which may be included within the spirit and scope of the invention.

Example I

Transmission Analysis

Figure 3:
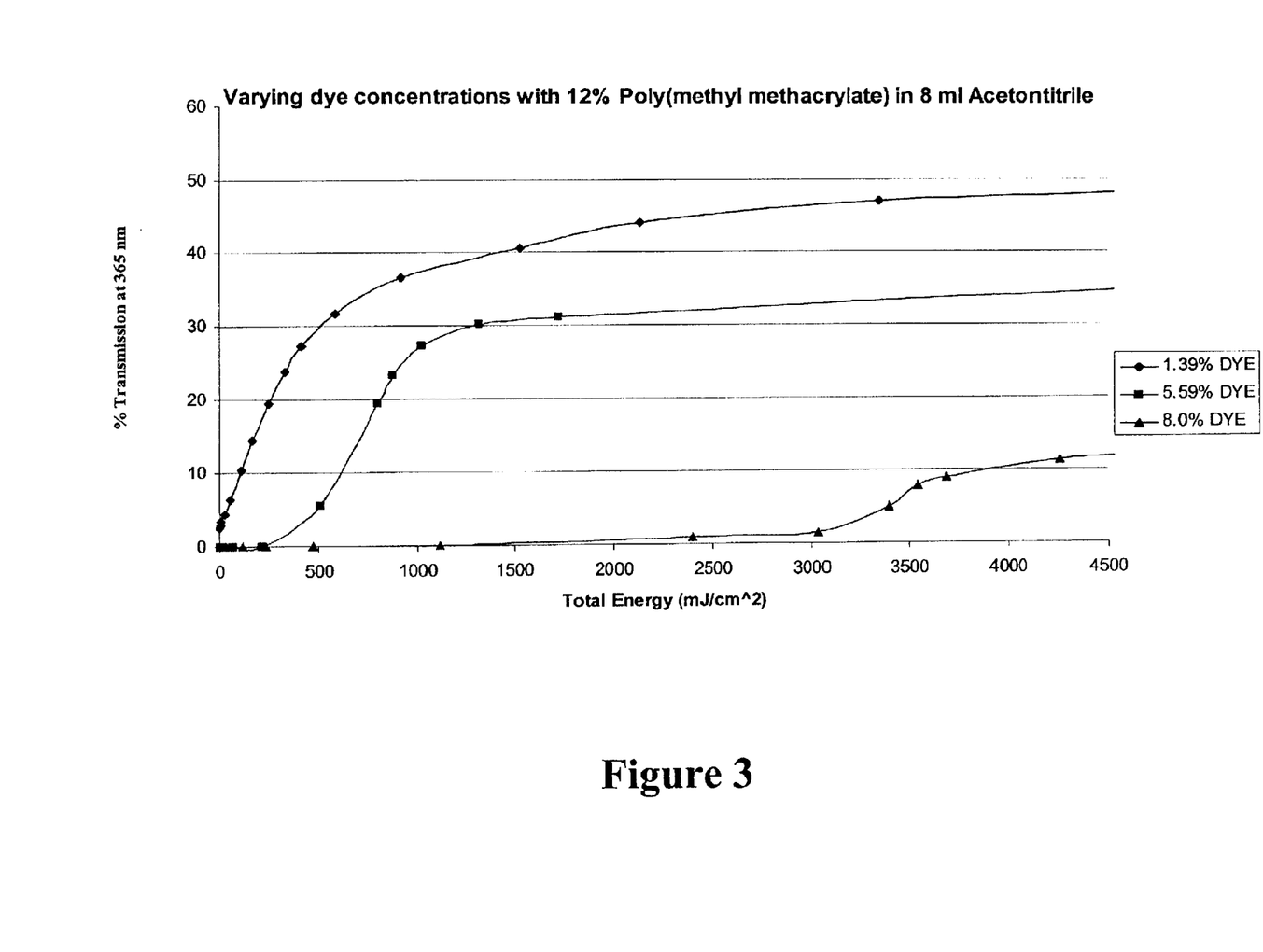
FIG. 3 is a graph of the bleaching rate of contrast enhancement layers comprising pyrylium dye.
Figure 4:
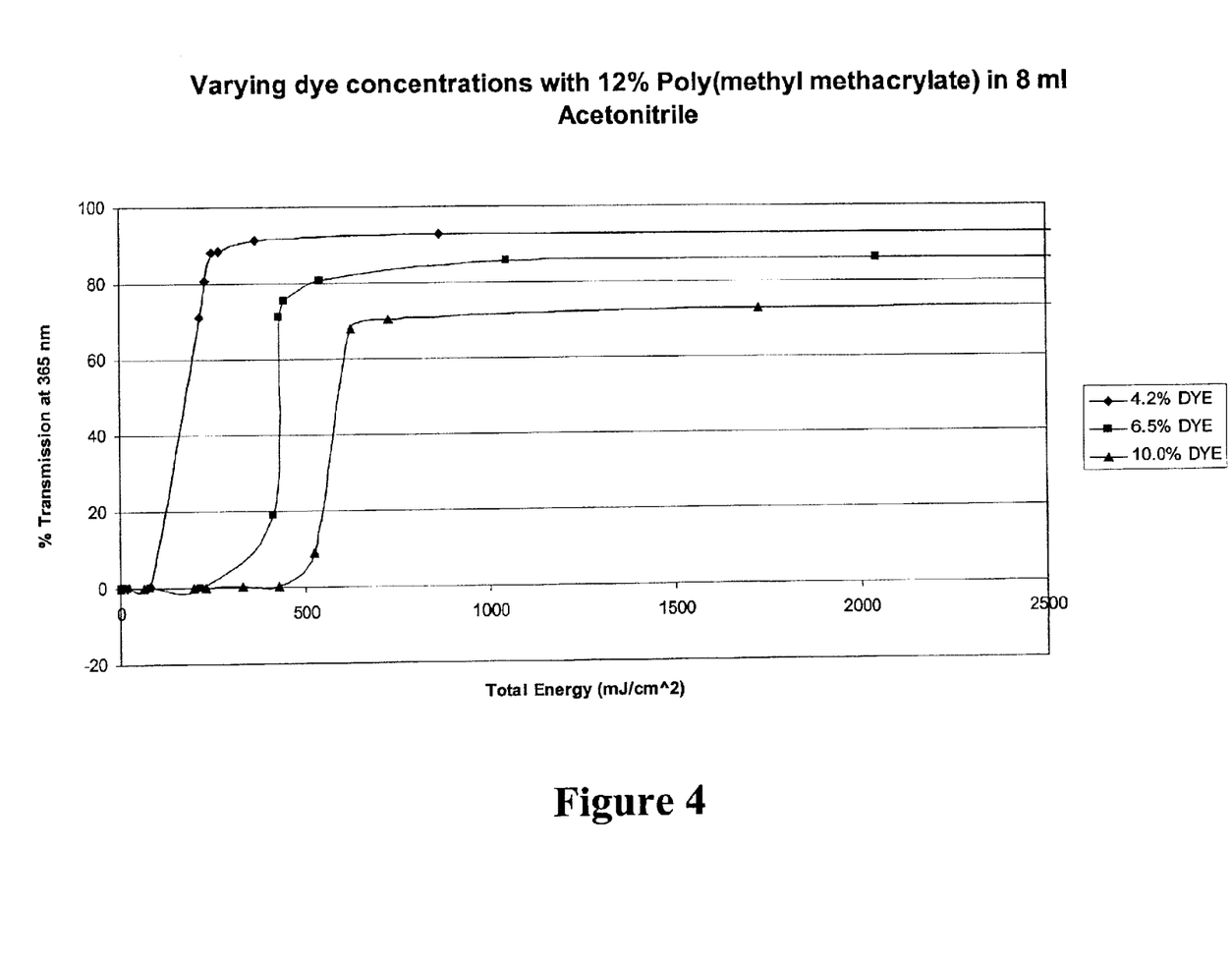
FIG. 4 is a graph of the bleaching rate of contrast enhancement layers comprising diazonium dye.

A CEM layer containing varying concentrations of either pyrylium dye or diazonium dye was spin coated on a glass substrate at 2000 rpm for 30 seconds producing a film thickness of approximately 0.5 microns. The surface was baked at 85° C. for 3 minutes. The slide was then irradiated with 365 nm light at a given power for a period of time. The percent transmission was measured after irradiation. FIGS. 3 and 4 are plots of the energy applied (in $mJ/cm^2$) (X axis) vs. percent transmission at 365 nm (Y axis), producing a graph of the bleaching rate.

Pyrylium dye was mixed with diallyl thiourea at a 4:1 molar ratio of diallylthiourea to the pyrylium dye and dissolved in 15% Poly(methyl methacrylate) in 8 ml of Acetonitrile. FIG. 3 depicts the bleaching rate of three different concentrations of pyrylium dye. The pyrylium dye was added to final concentrations of 1.39%, 5.59%, and 8.0%. As expected, the lowest concentration (1.39%) had the highest percent transmission at just under 50% at 4500 mJ/cm2. The experiment was carried out to a maximum exposure of 300 J at which point 70% transmission was reached (data not shown). The 5.59% concentration reached 35% transmission at 4500 mJ/cm2 this exposure was carried out to a maximum exposure of 700 J at which point 70% transmission was reached. The 8.0% dye concentration reached just over 10% transmission at 4500 mJ/cm2 and 55% transmission at 700 J.

Diazonium dye was dissolved in 12% Poly(methyl methacrylate) in 8 ml acetonitrile. FIG. 4 depicts the bleaching rate of three different concentrations of diazonium dye. The diazonium dye was added to final concentrations of 4.2%, 6.5%, and 10%. Again the lowest concentration yielded the highest percent transmission, although transmission with the diazonium dye required considerably less energy than with the pyrylium dye. The 4.2% dye reached 90% transmission at less than 500 mJ/cm2. The 6.5% dye reached approximately 85% transmission at 1000 mJ/cm2 and the 10% dye reached over 70% transmission at 1000 mJ/cm2.

Example II

Photokinetic Analysis

A MeNPOC monomer was covalently attached to a solid support. A CEM layer comprising diazonium dye was then spincoated on the solid support. The surface was baked at 85° C. for 3 minutes. The support was then selectively deprotected by irradiation through a mask at 365 nm. The mask was then translated horizontally over an adjacent region for a subsequent, longer exposure. The CEM was removed by washing the surface with acetonitrile. The pattern of the resulting surface deprotection was then "stained" by coupling a fluorescein phosphoramidite to the surface. The measured fluorescein intensity is proportional to the amount of MeNPOC removed, and thus the rate of surface photolysis. The experiment was repeated for various concentrations of diazonium dye.

Figure 5:
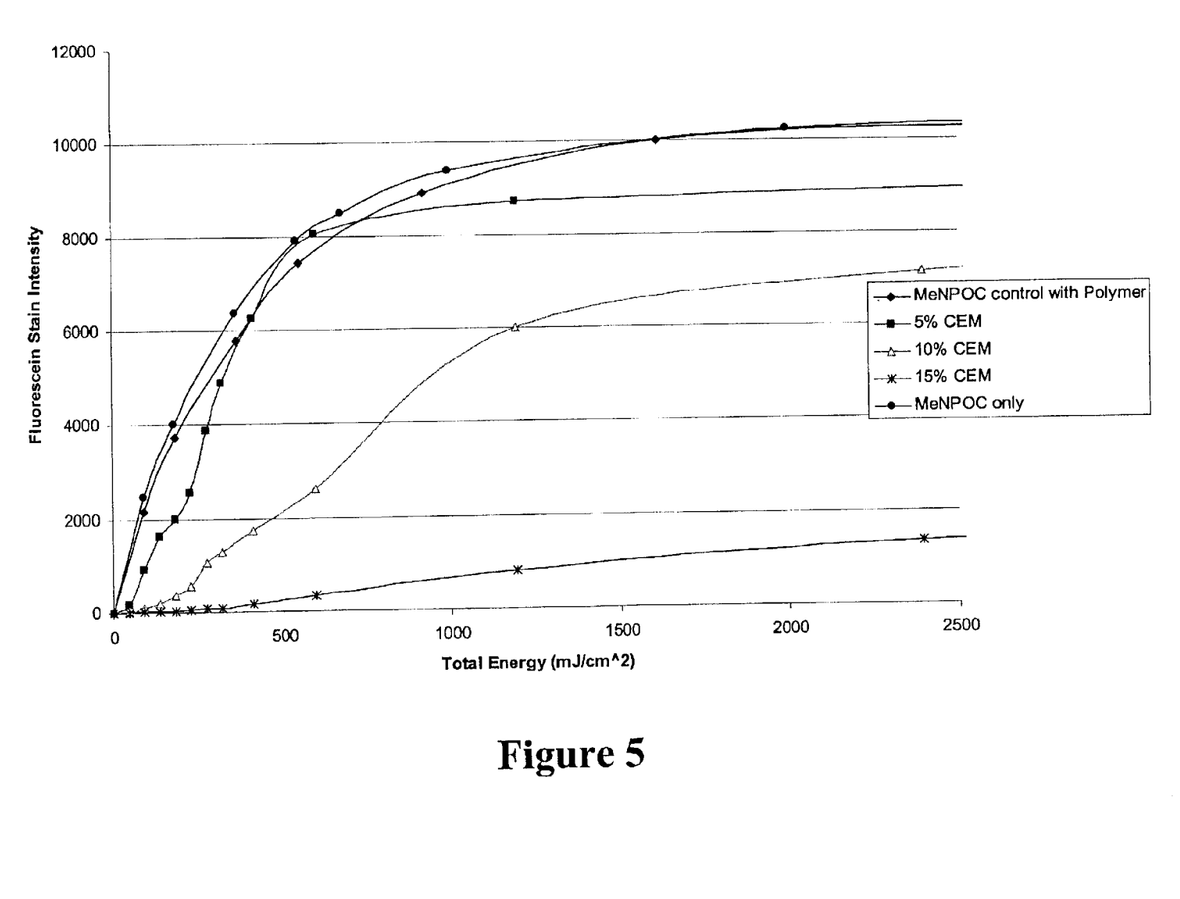
FIG. 5 is a graph of the photokinetic response of removal of the photolabile MeNPOC protecting group through the contrast enhancement layer comprised of a diazonium dye spincoated on top of a MeNPOC containing surface.

FIG. 5 depicts the results of the above experiment. The X axis is the Total Energy used in $mJ/cm^2$. The Y axis is the Fluorescein Stain Intensity (FSI). The "MeNPOC only" serves as the baseline, thus the maximum FSI is approximately 10000 units. The curves of the "polymer alone" and the "MeNPOC control with polymer" are nearly identical to that of the "MeNPOC only" curve, thus indicating that the latency effect is not created by addition of the polymer, but is rather due to the addition of the dye. The FSI for the 5% solution reached nearly 9000 units at 1000 mJ/cm2, which is consistent with the bleaching rate results from FIG. 4. The FSI for the 10% solution reached approximately 7000 units at 2000 mJ/cm2, which is again consistent with the bleaching rate results from FIG. 4. The FSI of the 15% solution was approximately 1000 units at 2000 mJ/cm2.

Example III

Lithographic Evaluation

Figure 6:
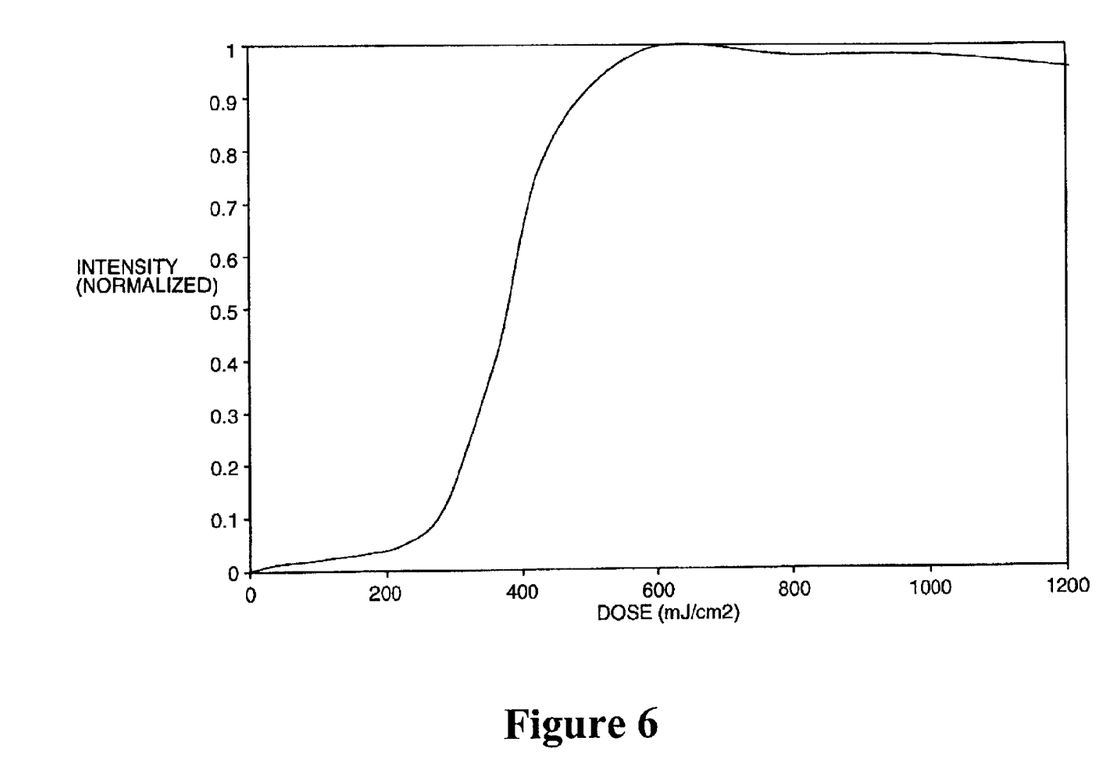
FIG. 6 is a graph of the nonlinearilty of the response of photoresist to radiation exposure.

As shown in FIG. 6, the high contrast observed in photo processes reflects the nonlinearity of the response as a function of the irradiation dose. In traditional photo resists, this nonlinearity stems from the solubility behavior of the polymer. Although the catalytic photo process described in this application does not involve a development step, non-linear behavior was observed. This probably results from a titration effect: a quantity of acid must accumulate before the DMT group is removed.

The lithographic behavior of the process was evaluated by spin coating a 0.5 μm thick film of poly (methyl methacrylate) (PMMA) containing the nitrobenzyl ester PAC (0.5 wt %) and the enhancer (8 wt %) having the following structures:

Photo Activated Catalyst (PAC)

Enhancer onto a glass substrate bearing covalently bound polynucleotides whose terminal 5' hydroxyl groups were DMT protected. The coated substrate was prebaked at 85° C. for 2 min, irradiated with varying doses at 365 nm, and postbaked at 85° C. for 2 min. The polymer coating was then removed with an acetone wash and the surface treated with a fluorescent coupling reagent. As shown by the sensitivity curve in FIG. 6, the lithographic process generated a direct image with a sensitivity of 600 mJ/cm$^2$ at 365 nm and a contrast of 3.0. By increasing the concentration of the PAC, the sensitivity of the system can be significantly improved. However, this may result in a decrease in the contrast. The contrast was calculated using the contrast equation as defined in Reiser, Arnost, Photoreactive Polymers: the Science and Technology of Resists, pp. 226–228 (1989), incorporated in its entirety herein by reference for all purposes.

Figure 7:
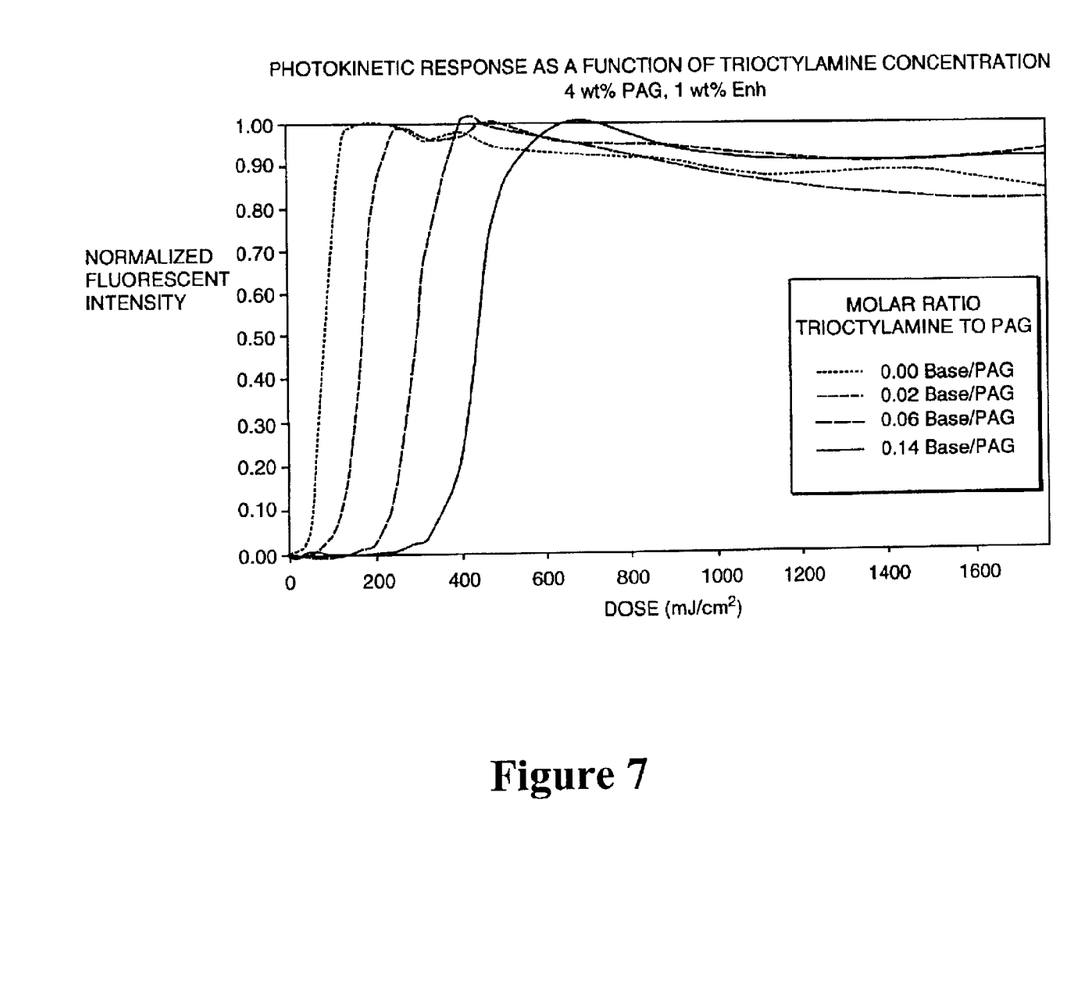
FIG. 7 is a graph of the photokinetic response of the resist containing PAG and enhancer as a function of trioctylamine concentration.

In addition to tuning the sensitivity and the contrast by altering the concentration of the PAC and the enhancer, it is also possible to affect these two properties by adding an amine to the formulation to improve environmental stability and resolution of the resist. Photokinetic response was measured as a function of the concentration of trioctylamine. As shown in FIG. 7, the dose required to reach complete detritylation increased with increasing concentrations of trioctylamine (increasing from 130, 240, 400, and 650 mJ/cm$^2$ for added base of 0.0, 0.08, 0.24 and 0.56 wt % respectively. A CEM may also be added to the resist to further modulate the response.

CONCLUSION

The presently claimed invention provides greatly improved methods for synthesizing arrays of diverse polymer sequences. Many variations of the invention will be apparent to those of skill in the art upon reviewing the above description. It is to be understood that the above description is intended to be illustrative and not restrictive. Therefore, it is to be understood that the scope of the invention is not to be limited except as otherwise set forth in the claims.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method for synthesizing and introducing latency into the synthesis of a polymer array, said polymer array selected from the group consisting of an oligonucleotide array and a peptide array, on a substrate comprising the steps of:

a) providing a surface having one or more synthesis intermediates bound thereon, said synthesis intermediates selected from the group consisting of a linker, a nucleotide, an amino acid, a peptide and an oligonucleotide, and the synthesis intermediates having a reactive group protected from reaction by a first photosensitive protecting group, said first protecting group having a first wavelength of light which removes said protecting group from said reactive group;

b) coating said surface with a substance comprising a photobleachable compound, wherein said photobleachable compound absorbs light having said first wavelength;

c) irradiating at least a part of said surface with light having said first wavelength to:
        i) bleach said photobleachable compound; and
        ii) remove said protective group;

d) removing said substance from said surface;

e) reacting a subsequently added synthesis intermediate, said subsequently added synthesis intermediate selected from the group consisting of a linker, a nucleotide an amino acid, a peptide and an oligonucleotide, with the unprotected reactive group, the subsequently added synthesis intermediate having a reactive group protected from reaction by a second photosensitive protecting group, wherein said first and second photosensitive protecting groups are the same or different and said protecting group having a second wavelength of light which removes said protecting group from said reactive group, wherein said first and said second wavelengths of light are the same or different;

f) recoating said surface with a substance comprising a photobleachable compound, wherein said photobleachable compound absorbs light having said second wavelength; if another synthesis intermediate is to be added; and g) repeating steps b) through f) or not, until the desired polymer array is obtained.

2. The method of claim 1 wherein said synthesis intermediate is a nucleotide.

3. The method of claim 1 wherein said synthesis intermediate is a polynucleotide.

4. The methods of claim 1 wherein said synthesis intermediate is an amino acid.

5. The method of claim 1 wherein said photobleachable compound is a photobleachable dye.

6. The method of claim 5 wherein said photobleachable dye is pyrylium dye or diazomium dye.

* * * * *